(12) United States Patent
Gill et al.

(10) Patent No.: US 8,032,307 B2
(45) Date of Patent: Oct. 4, 2011

(54) METHODS AND APPARATUS FOR GENOTYPING

(75) Inventors: Peter Gill, Birmingham (GB); Lindsey Dixon, Birmingham (GB)

(73) Assignee: Foresnic Science Service Ltd., London (GB)

( * ) Notice: Subject to any disclaimer, the term of this patent is extended or adjusted under 35 U.S.C. 154(b) by 726 days.

(21) Appl. No.: 11/937,825

(22) Filed: Nov. 9, 2007

(65) Prior Publication Data
US 2008/0161196 A1    Jul. 3, 2008

Related U.S. Application Data

(63) Continuation of application No. 10/408,961, filed on Apr. 8, 2003, now abandoned.

(30) Foreign Application Priority Data

Apr. 11, 2002 (GB) .................................. 0208364.0

(51) Int. Cl.
*G01N 33/48* (2006.01)
(52) U.S. Cl. ......................................................... 702/19
(58) Field of Classification Search ...................... 702/19
See application file for complete search history.

(56) References Cited

U.S. PATENT DOCUMENTS

| 6,342,355 | B1 | 1/2002 | Hacia et al. |
| 2002/0016680 | A1 | 2/2002 | Wang et al. |

FOREIGN PATENT DOCUMENTS

WO    WO 02/03849 A2    1/2002

OTHER PUBLICATIONS

Sohni et al., "Active electronic arrays for genotyping of NAT2 polymorphisms," *Clinical Chemistry* (2001) 47 (10): 1922-1924.
Gill et al., "A new method of STR interpretation using inferential logic—development of a criminal intelligence database," *International Journal of Legal Medicine* (1996) 109: 14-22. XP001104965.
International Search Report for corresponding International Application PCT/GB2003/01489 mailed May 6, 2004.

*Primary Examiner* — Jerry Lin
(74) *Attorney, Agent, or Firm* — Merchant & Gould P.C.

(57) ABSTRACT

A method for establishing the genotype of the locus is provided in which a series of calibration samples are analysed, the results being one of three indication types, a window being defined relative to the indication for each of the indication types, unknown samples being similarly analysed with the window that they fall within being taken to determine the indication type for the unknown sample and hence the genotype of the relevant locus. The technique provides a robust, reliable and accurate method of genotyping which is suited to automation.

22 Claims, 1 Drawing Sheet

METHODS AND APPARATUS FOR GENOTYPING

CROSS REFERENCE TO RELATED APPLICATIONS

Figure 1:
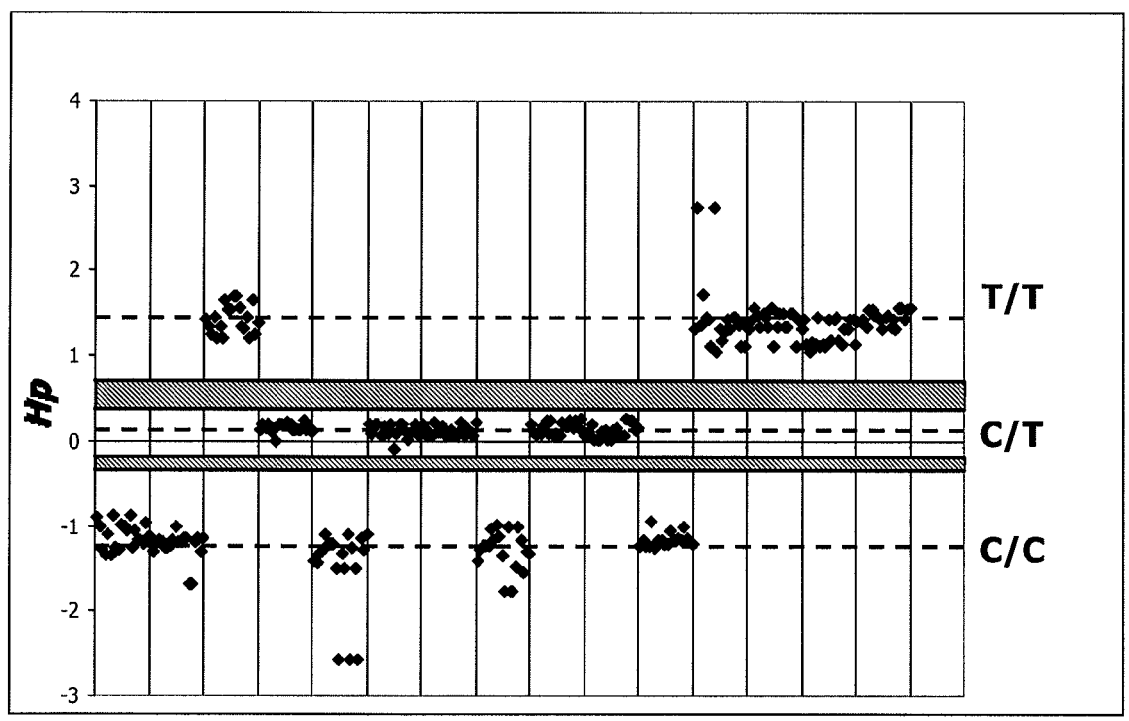

This application is a Continuation Application of U.S. application Ser. No. 10/408,961, filed Apr. 8, 2003 now abandoned, which claims benefit of Ser. No. 0208364.0, filed Apr. 11, 2002 in the United Kingdom and which application(s) are incorporated herein by reference. A claim of priority to all, to the extent appropriate is made.

This invention concerns improvements in and relating to methods and apparatus for genotyping, particularly, but not exclusively, in relation to forensic and other applications where rigorous and reliable genotype results are required.

Genotyping based on the consideration of single nucleotide polymorphisms, SNPs, at loci is finding increasing application. The principal developments to date have been in relation to medical applications, such as the diagnosis of genetic based conditions, where the identity of the SNP base at a locus is considered. One identity is generally considered normal with the other being indicative of the condition in such cases. A single or low number of loci are generally involved in such considerations as the occurrence of the SNP identity indicating the condition is, by its very nature, a rare occurrence. The principal interest is in a yes/no style answer as to whether the condition indicating SNP identity is present or not.

Forensic applications rely upon the use of loci for which there is a reasonable possibility of either SNP identity for the particular locus occurring. To provide the discriminating power between individuals a significant number of such loci must, therefore, be considered.

To provide a practical system the applicant is developing multiplex systems which allow a large number of loci to be amplified and probed simultaneously in a single sample. It is also desirable to be able to automate the consideration of samples in forensic applications. In any forensic technique the consideration most be accurate, reliable and robust.

The present invention has amongst its aims the provision of techniques which are quantitative and/or robust and/or suited to automation.

According to a first aspect of the present invention we provide a method of establishing the genotype at a locus, the genotype being one of two possible identities, the method including:

analysing one or more calibration samples to provide an indication of the genotype at one or more loci, the indication for a given locus including a measure of the presence of the first possible identity and a measure of the second possible identity;

providing a window relative to the indication for a given locus;

analysing an unknown sample to provide an indication of the genotype at a locus for which a window is provided, the indication including a measure of the presence of the first possible identity and a measure of the second possible identity for that given locus;

the indication for a locus for the unknown sample being compared with the window for that locus, that analysis of the unknown sample for that locus being accepted if the indication is within the window and/or that analysis of the unknown sample for that locus being rejected if the indication is outside the window, the genotype for a locus being derivable from the indication.

Preferably the single nucleotide polymorphism based genotype is considered at a locus.

Preferably the analysis of the calibration samples and/or unknown sample and/or control samples involves PCR based amplification. Preferably micro-fabricated arrays are used. Preferably the analysis involves the use of identity selective probes.

The method may establish the genotype for at least 2, preferably at least 4, more preferably at least 8 and ideally at least 12 loci in respect of the calibration samples and/or unknown samples and/or control samples and most preferably all.

The method may include analysing a plurality of calibration samples. Preferably at least 5, more preferably at least 10 and ideally at least 15 calibration samples may be analysed. Between 10 and 40 calibration samples may be analysed.

A single replicate may be considered for each calibration sample, but more preferably a plurality of replicates are considered. At least 5, more preferably at least 10 and potentially 15 or more replicates may be considered, ideally for each sample.

The indication may be the level of one or more distinctive components introduced into the results of the amplification of the sample. The distinctive components may be dyes, preferably dyes attached to selective probes. Preferably one dye is attached to a probe which selectively hybridises in the presence of one identity and a different dye is attached to a probe which hybridises in the presence of the other identity. The indication may be the ratio of the measured amount of one distinctive component relative to another distinctive component. The indication may be log (level of one dye/level of the other dye). The level of one distinctive unit may provide the measure of the first identity. The level of another distinctive unit may provide the measure of the second identity. The level may be measured by an instrument.

The indication, for any replicate and/or any sample, may be one of three indication types. Preferably one indication type relates to one homozygous possibility for the genotype, a second indication type relates to the heterozygous possibility for the genotype and the third indication type relates to the other homozygous possibility. Preferably the second indication is generally intermediate the first and third in terms of the measure.

A plurality of indications for a sample and/or an indication type may be used to generate an average indication. The average may be expressed as a mean, but is more preferably a median. The window may be defined relative to an average indication. Preferably three windows are defined, each relative to an average indication for each of the three indication types.

The window may be defined in terms of a statistical based parameter relative to the indication. The window may be defined in terms of a multiple, including fractions, of a standard deviation. The window may be defined in terms of a multiple, including fractions of the indication itself. The window may have defined upper and lower limits, particularly for heterozygous genotypes. The window may be open ended in one direction, particularly for homozygous genotypes.

The window for one locus may be defined in a different way to the window for another locus. The definition may differ in terms of the type of parameter used. The definition may differ in terms of the value of the parameter used. The window may be equal in extent to either side of the indication or may be unequal.

Where a plurality of windows are provided they may be discrete relative to one another or may overlap in one or more cases. The windows defined from the indication or average indication for the heterozygous indication type may overlap with one or both of the windows for the homozygous types. Preferably both homozygous windows are discrete from one another.

The method may include analysing a plurality of unknown samples. Preferably at least 5, more preferably at least 10 and ideally at least 15 unknown samples may be analysed. Between 10 and 40 samples may be analysed.

A single replicate may be considered for each unknown sample, but more preferably a plurality of replicates are considered. At least 5, more preferably at least 10 and potentially 15 or more replicates may be considered, ideally for each unknown sample.

Preferably the indication for the unknown sample is expressed in an equivalent way to the indication for the one or more calibration samples.

A plurality of indications for an unknown sample may be used to generate an average indication. The average may be expressed as a mean, or more preferably as a median. The average indication for the unknown sample may be compared with the window or windows.

The indication for the unknown sample may be compared with a window by comparing the value of the indication with the range of values defining the window. A comparison against each window may be made. If the value of the indication for the unknown sample is within the range of a window preferably that analysis of the unknown sample is accepted and ideally the indication gives the genotype. If the value of the indication falls within the range for two windows then preferably that analysis is rejected. If the value of the indication falls outside the range of any window then preferably that analysis is rejected.

Preferably the genotype is derivable from the indication or average indication based on the measure. A higher measure for one identity relative to the other may indicate a homozygous identity in favour of that identity. A generally equal measure for the two identities may indicate a heterozygous identity.

According to a second aspect of the present invention we provide a method of establishing the genotype at each of a plurality of loci, the genotype at each locus being one of two possible identities, the method including:

analysing a plurality of replicates of each of a plurality of calibration samples to provide an indication of the genotype at each of the loci for each replicate of each sample, the indication being a ratio of a measure of the presence of the first possible identity relative to a measure of the second possible identity for a given locus, the indication for a sample at a given locus being one of three indication types;

generating an average indication for each of the three indication types from the indications in each of those indication types;

providing a window relative to the average indication for each of the three indication types for each of the loci;

analysing a plurality of replicates of an unknown sample to provide an indication of the genotype at each of the loci for which a window is provided, the indication being a ratio of a measure of the presence of the first possible identity relative to a measure of the second possible identity for that given locus;

generating an average indication from each of the indications for the replicates of that unknown sample for each of the loci;

comparing the average indication for the unknown sample at a locus with the windows provided for that locus, the analysis of the unknown sample being accepted if the indication is within a window and/or the analysis of the unknown sample being rejected if the indication is outside the window, the genotype for a locus being derivable from the average indication.

The first and/or second aspects of the invention may include any of the features, options or possibilities set out elsewhere in this document and in particular from amongst the following.

Preferably the genotype or genotypes established for the unknown sample or samples are used in forensic applications. The genotype or genotypes may be used as evidence in criminal or civil proceedings and/or may be used in an investigation by a law enforcement agency.

The method is preferably automated. The method is preferably performed by an expert system. The automation and/or expert system may include the amplification of the samples and/or the probing of the samples and/or the determination of the indication and/or the provision of the windows and/or the comparison and/or the establishment of the genotype, and ideally all of these steps.

The method may be performed on a micro-fabricated array. Preferably a plurality of calibration samples and/or unknown samples and/or control samples are considered on a single micro-fabricated array. Preferably a plurality of replicates of the samples may are considered on a single micro-fabricated array.

Preferably the calibration samples are analysed and/or windows are provided for each performance of the method. The calibration sample indications and/or windows from one performance of the method may be used in later tests for establishing genotypes, but this is not preferred.

Preferably the method is used to establish the windows for each loci, ideally during each run of the method.

The method may include one or more controls or verifications. The method may include analysing one or more control samples to obtain a control indication, the control indication including a measure of the suggestion of the first possible identity and a measure of the suggestion of the second possible identity, preferably the ratio between those suggestions. The indication may be presented in an equivalent way to the indication for the calibration and/or unknown samples. The control sample may be a reverse primer, for instance for the amplification process, for that locus. Control samples for each locus may be employed. Preferably an average for the indication for the control sample is obtained, for instance a median. The control indication may be used to ensure the indication is of a sufficient level for the analysis to be considered. The control indication may be used to set a threshold. The threshold may be set at an absolute level or may be set at a relative level against the control indication or the average therefore. The threshold may be expressed as a multiple, including fractions, of a number of standard deviations above the control indication or average therefore. A sample or replicate falling below the threshold may be discounted from further consideration. The sample or replicate may be discounted with respect to that or all loci.

Preferably the method includes analysing a plurality of control samples. Preferably at least 5, more preferably at least 10 and ideally at least 15 control samples may be analysed. Between 10 and 40 samples may be analysed.

A single replicate may be considered for each control sample, but more preferably a plurality of replicates are considered. At least 5, more preferably at least 10 and potentially 15 or more replicates may be considered, ideally for each control sample.

The method may be used to establish genotypes in respect of samples which involve DNA from more than one source.

The method may be used to establish genotypes in respect of mixtures where the proportions contributed are uneven.

Various embodiments of the invention will now be described, with reference to accompanying FIG. 1, in which a plot of $H_P$, where $H_P = \log(cy5a/cy5b)$, for twenty replicates for each of 15 individuals is provided.

Forensic applications of genotyping require an accurate and robust determination of a genotype to be made by any analysis technique.

SNP based analysis is being developed for use in forensic applications. This involves the determination of the SNP identity of the base at a loci from amongst the two possible identities. Unlike medical analysis where the interest is in the occurrence of the SNP identity which is rare for a locus, compared with the common identity, forensic based techniques require the loci to be ones for which both SNP identities have a significant chance of occurrence. To provide the ability to distinguish between one individual and another in such cases a significant number of loci need to be considered in combination with one another to generate the genotype.

To facilitate the automated analysis of SNP loci microfabricated arrays can be used. Their use involves placing a part of the sample to be genotyped in a well in the array. The DNA of the sample is then subjected to an amplification regime to increase the amount of informative DNA present, DNA containing the SNP locus. The amplified sample is then contacted with two probes for a particular SNP locus. One probe selectively hybridises to the DNA in the case of one of the SNP identities, whilst the other probe hybridises in the case of the other identity. Because the amplified DNA is tethered, the well can then be washed to remove the non-hybridised probe for a given locus. The two probes carry different identity indicating units, generally dyes. The well is then analysed by an instrument to reveal dye present and hence the SNP identity for the locus.

As for forensic applications it is necessary to conduct analysis of the SNP identities at a large number different loci the applicant has developed multiplex analysis. SNP identities, primers and probes suitable for this purpose have been developed by the applicant. This allows a DNA sample to be amplified, contacted with suitable probes and hybridised in a single well reaction in respect of a large number of loci simultaneously. In those cases each SNP has two probes with distinctive units for each probe. Consideration of the colours detected indicates the base at each SNP under consideration.

To be truly reliable for forensic applications, include use as evidence in a court of law, the genotype considered as being indicated by the analysis must be robust. The yes/no type answer used in medical diagnosis has been established by the applicant to be insufficient. Hence the applicant has developed a quantitative analysis towards this aim. To extend this quantitative analysis further and make it suitable for automation and ideally incorporation into an expert system whilst achieving sufficient standards in reliability and consistency of interpretation the applicant has developed the techniques of the present invention. In developing these techniques it is also necessary to bear in mind that compared with medical applications, where the sample to be tested is collected direct from the person of interest under controlled conditions, the samples in forensic contexts may be less than perfect for a variety of reasons. For instance, the sample collected may be small and/or aged and/or a mixture of DNA from more than one source and are indirectly collected. Any expert system must therefore be able to cope with all of these issues at yet be reliable and robust.

Whilst the principal of the technique is described below in relation to a single locus it should be appreciated that in practice multiple loci will generally be considered. That requirement simply involves a repeat consideration of the principals outlined in relation to each locus.

The basic consideration for any given locus is to determine the genotype for that locus. In the case of SNP based considerations, the genotype has one of three possibilities. If the SNP identities are designated a and b then the possible identities are aa or bb for homozygous persons and ab for heterozygous persons. To determine the genotype for a locus with two alleles, designated a and b, the signals from the measurement of the dyes for the two probes are considered. These may be, for example, -cy5 signals arising from the hybridisation of the respective probes for the two SNP identities, $cy5_a$ and $cy5_b$. The ratio of these two dye signals represents an indication and may be used to express the allele identity analysed in terms of a proportion, $H_p$, where:

$$H_p = \log_{10}\left[\frac{cy5_a}{cy5_b}\right] \quad 1)$$

As there are 3 possible genotypes: aa, ab and bb the indication should falls into one of three indication types. A probe complementary to a homozygote sample aa produces the biggest signal, whereas the signal is at background level for the alternative bb homozygote. A heterozygote ab gives an intermediate signal. The converse signal levels of course apply when hybridised against the probe to allele b.

The nature of the samples under consideration, the need to test mixed samples, potentially low levels of DNA all give rise to variations in the measured outcome compared with this theoretical division. Thus rather than just conduct a single test for a sample and establish the dominant colour in the signal and hence the SNP identity, as is the case in medical diagnosis considerations, a far more detailed and rigorous approach is proposed.

As a calibration step the technique considers a number of calibration samples taken from known individuals under controlled conditions. The genotype results obtained are highly reliable as a result. For each individual a number of replicates are performed and an indication, a $H_p$ value, is obtained for each. These $H_p$ values are then taken together to give a median $\overline{H_p}$ for the individual. The numbers considered can vary, but in this example the median $\overline{H_p}$ for each of 15 individuals was determined, based on 20 replicates in each case.

As can be seen in FIG. 1 each of the individuals gave a genotype that fell into one of the three indication types anticipated. The replicates (diamond symbols) for one individual are separated from the next by the vertical lines. FIG. 1 demonstrates that the proportions were approximately constant for each genotype. Even with such good samples, however, some variation between replicates was encountered. To address this issue of potential variation these calibration results form the basis of a calibration against which unknown samples can be compared. To allow rigorous interpretation of unknown samples in an expert system the variation in the replicates from the calibration results is used to define windows for each of the three general groupings referred to above.

In the worked example, windows for each genotype were calculated based around the indication type, using a definition of $\overline{H_p} \pm 3SD$ for heterozygotes, and with homozygotes being either $< \overline{H_p} + 3SD$ or $> \overline{H_p} - 3SD$ depending on which homozygotic identity was involved, SD being standard deviations. The actual size of the windows, therefore, depends on the variations between replicates for the calibration results The applicant has established that ideally the three windows do not overlap each other, as shown in FIG. 1, but this does not preclude the window for heterozygotes overlapping with either homozygote window. The boundaries of the windows are shown in FIG. 1 by solid lines, with the shaded areas being outside the windows.

The particular example of FIG. 1 refers to the TSC0869795 locus and the genotypes are C/C; C/C; T/T; C/T; C/C; C/T; C/T; C/C; C/T; C/T; C/C; T/T; T/T; T/T; T/T respectively for the calibration results.

Using these windows interpretation of unknown samples is then possible. The unknown samples were analysed in the same way (amplification, hybridisation with probes and washing) using a number of replicates of the unknown sample in each case. In the case of non-overlapping windows, if an unknown genotype gives an $\overline{H}_p$ which falls within the window of a grouping it is determined to have that genotype; if it falls outside any of the windows it is deemed inconclusive. In the case of overlapping windows a similar approach is taken, but in this case unknown genotypes falling within the overlap are also deemed inconclusive.

Windows are determined and unknown samples then considered in this way for each of the loci. Different window forms and/or sizes may be appropriate for different loci.

As with the calibration, the genotyping of the unknown samples uses a number of replicates to increase reliability of the results. As both calibration and unknown sample genotyping are based on repeat analysis an improvement in reliability of the results is achieved. Furthermore, the use of windows allows effective consistent interpretation by expert systems without intervention on a basis that is rigorously supported.

The technique can be made more rigorous still through the use of controls.

Firstly negative thresholds can be determined to ensure that the signal, in the example a cy5 signal, were sufficiently strong to be subjected to the above mentioned genotyping process. This determination considers the cy5 signal arising from the hybridisation of the probe to the reverse primer (a control sequence). Again a median was determined by consideration of repeat controls and a threshold level was set on this basis. In the example the threshold was set at 6SDs above the median. If the dominant signal for an actual unknown sample falls below this threshold then it is deemed to be inconclusive and not considered further (this may be due to insufficient DNA being present, for example).

Separate negative controls of this type were performed for each locus.

To achieve the very best from the technique the calibration replicates, unknown replicates and control replicates for each locus to be considered in determining the genotype are handled in the same micro fabricated array. In this way calibration, unknown and control replicates and their respective results are used which have arisen under the same conditions. The applicant has established that there is sufficient inherent variation between amplification runs and/or between individual instruments to make this precaution advisable. When used in this way the calibration results are used to calculate the window positions and size on a run of an array by run of an array basis and the control results are similarly used on a run by run basis to establish the signal strength required to be considered. This ensures the windows and minimum signal threshold used are the most appropriate ones for the unknown samples being considered.

It is important for a quantitative test to be used for forensic applications. The use of a population of controls and samples in the technique gives a much better estimate than just a single result. The technique also clearly defines when a test is inconclusive by reference to the position of the median result of an unknown sample. Handling of signals that are too poor to be considered is also provided, i.e. those for which there is insufficient DNA to test.

It is important to note that the above mentioned techniques are not only applicable to samples containing DNA from a single source, but are also applicable to the analysis of mixtures.

The invention claimed is:

1. A method of establishing the genotype at each of a plurality of genetic loci, the genotype at each genetic locus being one of two possible identities, such that the genotype is heterozygous with respect to that identity or homozygous with respect to that identity, the method including:
   analysing a plurality of replicates of each of a plurality of calibration samples to provide an indication of the genotype at each of the genetic loci for each replicate of each calibration sample, the indication of the genotype being a level of one or more distinctive components, the indication being a ratio of a measure of the presence of the first possible identity relative to a measure of the second possible identity for a given genetic locus, the indication for a sample at a given genetic locus defining which one of three indication types the sample has at that given genetic locus;
   generating from the calibration samples an average indication for each of the three indication types from the indications in each of those indication types;
   providing an indication range relative to the average indication for each of the three indication types for each of the genetic loci;
   analysing a plurality of replicates of an unknown source sample to provide a indication of the genotype at each of the genetic loci for which an indication range is provided, the indication being a ratio of a measure of the presence of the first possible identity relative to a measure of the second possible identity for that given genetic locus;
   generating an average indication from each of the indications for the replicates of that unknown source sample for each of the genetic loci;
   comparing the average indication for the unknown source sample at a genetic locus with the indication ranges provided for that genetic locus, the analysis of the unknown source sample being accepted if the indication is within an indication range, an accepted analysis defining which one of three indication types the sample has at that given genetic locus and/or the analysis of the unknown source sample being rejected if the indication is outside the indication range, the genotype for a genetic locus being derivable from the average indication according to the indication range the indication for that genetic locus falls within.

2. A method according to claim 1 in which at least 10 replicates are analysed for each of at least 8 calibration samples, the genotype being established for at least 8 genetic loci, the indication being the level of one or more dyes, one indication type relating to one homozygous possibility for the genotype, the second of the indication types relating to the heterozygous possibility genotype, and the third indication type relating to the other homozygous possibility for the genotype.

3. A method of establishing the genotype at a genetic locus, the genotype being one of two possible identities, such that the genotype is heterozygous with respect to that identity or homozygous with respect to that identity, the method including:

analysing one or more calibration samples to provide an indication of the genotype at one or more genetic loci, the indication of the genotype being a level of one or more distinctive components, the indication for a given genetic locus including a measure of the presence of the first possible identity and a measure of the second possible identity;

providing a indication range relative to the indication obtained from the calibration samples for a given genetic locus;

analysing an unknown source sample to provide an indication of the genotype at a genetic locus for which an indication range is provided, the indication including a measure of the presence of the first possible identity and a measure of the second possible identity for that given genetic locus;

the indication for a genetic locus for the unknown source sample being compared with the indication range for that genetic locus, that analysis of the unknown source sample for that genetic locus being accepted if the indication is within the indication range and/or that analysis of the unknown source sample for that genetic locus being rejected if the indication is outside the indication range, the genotype for a genetic locus being derivable from the indication according to the indication range the indication for that genetic locus falls within .

4. A method according to claim 3 in which the method establishes the genotype for at least 12 genetic loci in respect of the calibration samples and unknown source samples.

5. A method according to claim 3 in which the method includes analysing at least 10 calibration samples.

6. A method according to claim 3 in which at least 10 replicates are considered for each sample.

7. A method according to claim 3 in which the indication is the level of one or more distinctive components introduced into the results of the amplification of the sample.

8. A method according to claim 3 in which the indication is the ratio of the measured amount of one distinctive component relative to another distinctive component.

9. A method according to claim 3 wherein the indication for the sample at a given genetic locus defines which one of three indication types the sample has at that given genetic locus, one indication type relating to one homozygous possibility for the genotype, a second indication type relating to the heterozygous possibility for the genotype, the third indication type relating to the other homozygous possibility.

10. A method according to claim 3 in which a plurality of indications for a sample and/or an indication type are used to generate an average indication, the average being expressed as a mean or as a median.

11. A method according to claim 3 in which the indication range is defined in terms of a multiple of a standard deviation.

12. A method according to claim 3 in which the indication range has defined upper and lower limits for heterozygous genotypes.

13. A method according to claim 3 in which the indication range is open ended in one direction for homozygous genotypes.

14. A method according to claim 3 in which a plurality of indications for an unknown sample are used to generate an average indication.

15. A method according to claim 3 in which the indication for the unknown source sample is compared with an indication range by comparing the value of the indication with the range of values defining the indication range.

16. A method according to claim 15 in which if the value of the indication for the unknown source sample is within the range of an indication range that analysis of the unknown source sample is accepted, if the value of the indication falls within the range for two quantity indication ranges then that analysis is rejected.

17. A method according to claim 15 in which if the value of the indication falls outside the range of any indication range then that analysis is rejected.

18. A method according to claim 3 in which the genotype is derivable from the indication or average indication based on the measure.

19. A method according to claim 3 in which the method is automated.

20. A method according to claim 3 in which the method is performed on a micro-fabricated array.

21. A method according to claim 3 in which the method includes analysing one or more control samples to obtain a control indication, the control indication including a measure of the suggestion of the first possible identity and a measure of the suggestion of the second possible identity in the form of a ratio between those suggestions, the control indication being used to ensure the indication is of a sufficient level for the analysis to be considered, the control indication being used to set a threshold, a sample or replicate falling below the threshold being discounted from further consideration.

22. A method according to claim 3 in which the indication range is defined in terms of a fractional multiple of a standard deviation.

* * * * *